United States Patent [19]

Cho et al.

[11] Patent Number: 5,414,156
[45] Date of Patent: May 9, 1995

[54] PROCESS FOR PRODUCING ORTHO-ISOPROPYLATED PHENOL DERIVATIVES

[75] Inventors: Jung H. Cho; Kie H. Nam; Wan S. Kim, all of Seoul, Rep. of Korea

[73] Assignees: Dong Kook Pharmaceutical Co., Ltd.; Ki-Beom Kwon, both of Souel, Rep. of Korea

[21] Appl. No.: 245,091

[22] Filed: May 10, 1994

[30] Foreign Application Priority Data

Sep. 8, 1993 [KR] Rep. of Korea ............... 1993-18007

[51] Int. Cl.$^6$ .................. C07C 37/50; C07C 37/11
[52] U.S. Cl. ................................ 568/781; 568/780
[58] Field of Search ..................... 568/780, 781

[56] References Cited

U.S. PATENT DOCUMENTS

| | | | |
|---|---|---|---|
| 2,831,898 | 4/1958 | Ecke et al. | 568/780 |
| 3,367,981 | 2/1968 | Napolitano | 568/781 |
| 4,447,657 | 5/1984 | Firth et al. | 568/783 |
| 5,175,375 | 12/1992 | Chang et al. | 568/781 |

FOREIGN PATENT DOCUMENTS 0258133 12/1985 Japan ..................... 568/781

Primary Examiner—Werren B. Lone
Attorney, Agent, or Firm—Morgan & Finnegan

[57] ABSTRACT

This invention relates to the process for producing ortho-isopropylated phenol derivatives having following general formula (VIII).

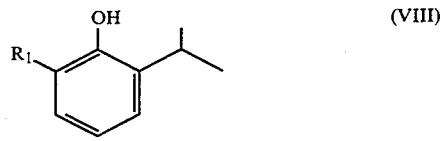

(in the above formula, $R_1$ is a hydrogen or a low alkyl group of $C_1$–$C_4$)

A process for producing ortho-isopropylated phenol derivatives (VIII) of the present invention is characterized by obtaining position isomer desired by means of Claisen rearrangement of phenyl allyl ether without catalyst in atmosphere, and then obtaining only one isomer by oxidation and reduction of the above-obtained position isomer. According to the present invention, ortho-alkylated phenol derivatives (VIII) having high purity at low temperature and low pressure can be prepared without producing a by-product and requirement of the complicated separation procedure.

12 Claims, No Drawings

PROCESS FOR PRODUCING ORTHO-ISOPROPYLATED PHENOL DERIVATIVES

This invention relates to a process for producing substituted phenol derivatives, more particularly, relates to the process for producing ortho-isopropylated phenol derivatives having following general formula (VIII) from phenyl allyl ether by means of Claisen rearrangement.

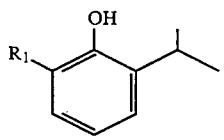
(VIII)

(in the above formula, $R_1$ is a hydrogen or a low alkyl group of $C_1-C_4$)

A typical example of ortho-isopropylated phenol derivatives having above general formula (VIII) is 2,6-diisopropyl phenol, (what is called, "Propofol") having narcotic influence and a number of method for producing 2,6-diisopropyl phenol have been suggested.

For example, U.S. Pat. No. 2,831,898 discloses a process for producing 2,6-diisopropyl phenol from propylene gas and phenol by Friedel-Crafts reaction at high pressure of 21-35 atm, high temperature of 200°-210° C. and under nitrogen atmosphere with aluminum phenoxide, as a catalyst, prepared from alumina and phenol. But there is a defect that 2,6-diisopropyl phenol desired was obtained only with 11.3% yield even though 2-isopropyl phenol which is a by-product was obtained with 31.4% yield.

U.S. Pat. No. 3,367,981 discloses the preparation method of a mixture of 2-isopropyl phenol and 2,6-diisopropyl phenol by heating of a mixture of phenol and propylene gas to 314° C. at nitrogen atmosphere in air-tight vessel on a transitional alumina, as a catalyst, prepared by heating of an aluminum oxide hydrate and further adding a propylene gas at 310°-312° C. after reducing a resultant pressure. This method has a defect that the yield of 2,6-diisopropyl phenol is low and the yield of 2-isopropyl phenol is high.

Also, U.S. Pat. No. 4,447,657 discloses the process for producing 2,6-diisopropyl phenol by contacting isopropyl (2-isopropyl phenyl) ether with fluorided alumina under nitrogen atmosphere at 150° C. and at 200 psig. This method uses the thermal rearrangement of alkyl phenyl ether. A drawback to this process is that interested 2,6-diisopropyl phenol has low yield and 2-isopropyl phenol and 2,4,6-triisopropyl phenol which are by-products have high yield.

These conventional processes suffer serious drawbacks since yield of 2,6-diisopropyl phenol is quite low and those processes require the injection of high pressure gas into vessel having high temperature and pressure, need to avoid contacting with air, and need to have complicated separation procedure because reaction product is a mixture of position isomers.

It is, therefore, an object of this invention to provide an improved process for producing the ortho-alkylated phenol derivatives (VIII) having high purity at low temperature and low pressure without producing a by-product and so that there is no requirement of the complicated separation procedure.

A process for producing ortho-isopropylated phenol derivatives of the present invention provided to achieve the above object is characterized by obtaining position isomer desired by means of Claisen rearrangement of phenyl alkyl ether without a catalyst in atmosphere, and then obtaining only one isomer by oxidation and reduction of the obtained position isomer.

In detail, the process for producing ortho-isopropylated phenol derivatives is comprised of following reaction steps for:

(a) producing a phenyl allyl ether having following general formula (III) by reaction of a phenol derivative having following general formula (I) and a crotyl derivative having following general formula (II),

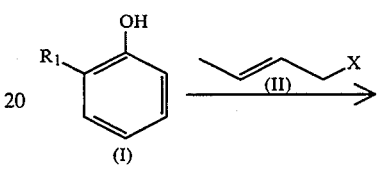

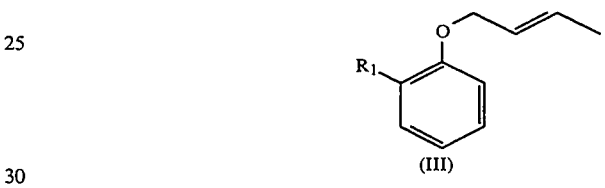

(in this reaction formula, $R_1$ is a hydrogen or a low alkyl group of $C_1-C_4$, X is chloride, bromide, iodide, para-toluene sulfonyl or methane sulfonyl)

(b) producing a phenol derivative having general formula (IV) where allyl group of the phenyl allyl ether (III) migrates to ortho position by means of Claisen rearrangement,

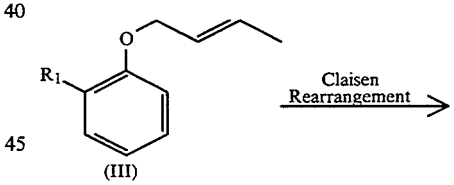

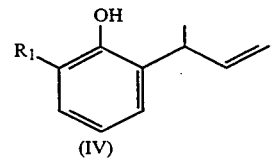
(IV)

(c) producing a hemiacetal having following general formula (X) by oxidation of the phenol derivative (IV), and

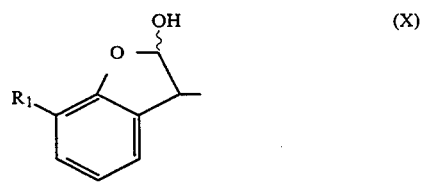

(d) producing an ortho-isopropylated phenol derivative (VIII) by reduction of the hemiacetal (X).

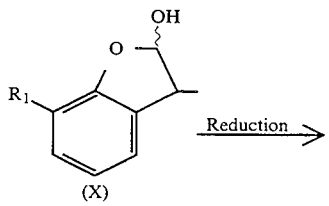

(X)

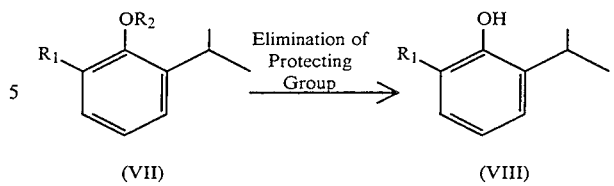

(VII) (VIII)

Hereinafter, the process of the invention will be further described in detail.

The step (a) where the phenol derivative having general formula (I) reacts with crotyl derivative (II) is occured in following base-solvent system and phenyl allyl ether (III) was obtained thereby: a base-solvent system consisting of potassium carbonate, sodium carbonate, potassium bicarbonate or sodium bicarbonate as a base and a polar solvent such as acetone, dimethylformamide or low alcohol as a solvent: a base-solvent system consisting of sodium ethoxide, sodium methoxide, sodium hydroxide, potassium hydroxide or lithium diisopropyl amine as a base and dry solvent such as tetrahydrofuran, ethyl ether, glyme, diglyme, low alkane or petroleum ether as a solvent: or a base-solvent system consisting of sodium ethoxide or sodium methoxide as a base and alcoholic solvent such as ethanol, methanol as a solvent.

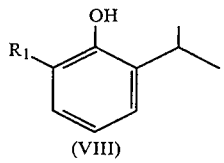

(VIII)

Also, according to the present invention, ortho-isopropylated phenol derivatives (VIII) may be produced by protecting —OH group of phenol derivatives (IV) obtained by migration of allyl group of the phenyl allyl ether (III) to ortho position by means of Claisen rearrangement prior to the oxidation reaction and then eliminating the protecting group after reduction by conventional method. That is, according to the invention, ortho-isopropylated phenol derivatives (VIII), may be prepared from phenol derivatives having general formula (IV) where allyl group is migrated to ortho position through following steps for:

(e) producing a phenyl ether derivative having following general formula (V) by protecting —OH group of the phenol derivative (IV) in which allyl group was migrated to ortho position, Claisen rearrangement (b) of phenyl allyl ether of general formula (III) is occured by heating with solvent such as diethylaniline, dimethylaniline, ethylene glycol, propylene glycol or trifluoroacetic acid or without solvent, and in result, phenol derivative having general formula (IV) was obtained by migration of allyl group to ortho position.

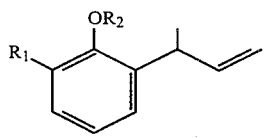

(in this formula, $R_2$ is methyl, acetyl, benzyl, trimethylsilyl or tert-butyldimethylsilyl as a protecting group of —OH group)

(f) producing an aldehyde having following general formula (VI) by oxidation of the phenyl ether derivative (V)

Into the producing the ortho-isopropylated phenol derivative (VIII) from the phenol derivative (IV), a protecting group may be introduced or not. When protecting group is not introduced, product (X) in the form of pentagonal hemiacetal was obtained by oxidation of phenol derivative (IV) produced by means of Claisen rearrangement. This oxidation reaction is occured in the presence of oxidizing agent such as ozone, osmium tetraoxide or potassium permanganate in a solvent such as acetic acid, mixture of acetic acid and acetonitrile, ethyl acetate, ethanol, methanol or chloroform. A hemiacetal derivative (X) is reduced into an ortho-isopropylated phenol derivative (VIII), object compound of the present invention, by means of Wolff-Kishner reduction, Clemmensen reduction or hydrogenation.

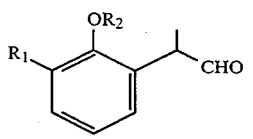

(g) producing a phenyl ether derivative having following general formula (VII) added isopropyl group onto ortho position by reduction of the aldehyde (VI), and When protecting group is introduced, a phenol derivative (IV) converts into a phenyl ether derivative (V) by protecting hydroxy group with methyl, benzyl, acetyl, tert-butyldimethyl silyl or trimethyl silyl, and a phenyl ether derivative (V) is oxidized into an aldehyde derivative (VI) in acetic acid, mixture of acetic acid and acetonitrile, ethyl acetate, ethanol, methanol or chloroform as a solvent in the presence of oxidizing agent such as ozone, osminum tetraoxide or potassium permanganate.

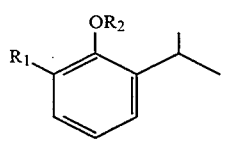

(h) producing an ortho-isopropylated phenol derivative (VIII) by eliminating protecting group from the phenyl ether derivative (VII).

The phenyl ether derivative (VII) is obtained by means of Wolff-Kishner reduction, Clemmensen reduction or hydrogenation of an aldehyde derivative (VI) and converted into a phenol derivative having general formula (VIII) by elimination of protecting group therefrom by conventional method.

For example, when the protecting group is methyl or benzyl group, it can be eliminated using trimethylsilyliodide, boron tribromide, borontrifluoride with thiol;

when the protecting group is tert-butyldimethylsilyl or trimethylsilyl, it can be eliminated using tetra-n-butyl ammonium fluoride in tetrahydrofuran, hydrogenfluoride aqueous solution, borontrifluoride, and when a protecting group is benzyl group, it can be eliminated by means of hydrogenation with palladium-on-charcoal as a catalyst, or sodium in liquid ammonia. The following examples are illustrative of this invention and are not to be construed as limiting the invention thereto.

EXAMPLE 1

2,6-diisopropylphenol was prepared by following reaction procedures.

1. The preparation of crotyl (2-isopropylphenyl) ether

In 30 ml of acetone, 5 g of 2-isopropyl phenol, 12.6 g of anhydrous potassium carbonate and 24.7 g of crotyl bromide were added with agitating. This mixture was further agitated for 24 hours at room temperature and 50 ml of water was added thereinto.

An organic layer was extracted from thus-obtained mixture twice with 50 ml of chloroform each time and washed with saturated sodium chloride aqueous solution. The extract was dried using anhydrous magnesium sulfate and then concentrated. 6.7 g of crotyl (2-isopropylphenyl) ether was obtained by separating the extract through a silica gel column chromatography with hexane/ethyl acetate (20:1) as a developing solvent.

NMR(CDCl$_3$): 1.29(6H, d, J=6.9), 1.80(3H, d, J=6), 3.40(1H, m), 4.50(2H, m), 5.57–5.87(2H, m), 6.88–7.26(4H, m)

2. Claisen Rearrangement

Crotyl (2-isopropyl phenyl) ether 6 g. was dissolved in 30 ml of diethylaniline and agitated at 200° C. for 24 hours and then cooled down to room temperature. The reaction mixture was dissolved in 100 ml of chloroform and washed three times with 65 ml of 1N hydrochloric acid each time. The resultant was dried with anhydrous magnesium sulfate and then concentrated.

Thus-obtained concentrate was separated through a silica gel column chromatography with hexane/ethyl acetate (20:1) as a developing solvent and thereby 2-(1-methyl-2-propenyl)-6-iso-propyl phenol 5.4 g was obtained.

NMR(CDCl$_3$): 1.30(6H, d, J=6.9), 1.46(3H, d, J=6), 3.30(1H, m), 3.68(1H, m), 5.21–5.34(3H, m), 6.06–6.20(H, m), 6.92–7.20(3H, m)

3. Introduction of protecting group 1 g of 2-(1-methyl-2-propenyl)-6-isopropyl phenol was dissolved in 15 ml of acetone and 1.45 g of anhydrous potassium carbonate and 2.66 g of benzylchloride were added thereinto with agitating. The mixture was agitated at 56° C. for 24 hours and cooled down to room temperature. 10 ml of water was added into the reaction mixture and organic layer thereof was extracted twice with 25 ml of methylene chloride each time and washed with a saturated sodium chloride aqueous solution. The resultant was dried with anhydrous sodium sulfate and concentrated.

Benzyl {2-(1-methyl-2-propenyl)-6-isopropylphenyl} ether 1.4 g was obtained by separating the concentrate through a silica gel column chromatography with hexane/ethyl acetate (30:1) as a developing solvent.

NMR(CDCl$_3$): 1.20(6H, d, J=6.9), 1.30(3H, d, J=6), 3.09–3.57(1H, m), 3.80–4.13(1H, m), 4.79(2H, b, s), 5.08(1H, m), 6.98–7.55(8H, m)

4. Oxidation

Benzyl {2-(1-methyl-2-propenyl)-6-isopropylphenyl} ether 1.6 g was dissolved in 10 ml of acetic acid and passed through ozone with agitating for 20 min in the rate of 60 mmol/hour at 15° C. 6 ml of water was added into this mixture and the mixture was cooled down to 0° C. and zinc powder 1.28 g was added thereinto. This reaction mixture was agitated for 1 hour and filtered. The filtrate was dissolved into 30 ml of methylene chloride and washed four times with 30 ml of 10% sodium bicarbonate each time and with water and saturated sodium chloride aqueous solution. The resultant was dried with anhydrous sodium sulfate and then concentrated.

2-(2-benzyloxy-3-isopropylphenyl) propanal 1.2 g was obtained by separating through a silica gel column chromatography with hexane/ethyl acetate (20:1) as a developing solvent.

NMR(CDCl$_3$): 1.23(6H, d, J=6.9), 1.35(3H, d, J=7.6), 3.40(1H, m), 4.01(1H, m), 4.80(2H, s), 6.76–7.60(8H, m), 9.54(1H, s)

5. Reduction 0.3 g of potassium hydroxide was added into 2 ml of propylene glycol and dissolved with agitating for 6 hours. Into this mixture. 0.18 g of 2-(2-benzyloxy-3-isopropylphenyl) propanal and 0.92 ml of hydrazine were added. This mixture was agitated for 12 hours at 80° C. and further agitated for 20 hours at 165° C. and then cooled down. Thus-obtained mixture was dissolved in 10 ml of water and 20 ml of ethylene chloride. Organic layer thereof was washed with water and saturated sodium chloride aqueous solution. The resultant was dried with anhydrous magnesium sulfate and then concentrated.

Benzyl (2,6-diisopropylphenyl) ether 121 mg was obtained by separating through a silica gel column chromatography with hexane/ethyl acetate (20:1) as a developing solvent.

NMR(CDCl$_3$): 1.22(12H, d, J=6.2), 3.38(2H, m), 4.78(2H, s), 7.07–7.56(8H, m).

6. Elimination of protecting group.

Benzyl (2,6-diisopropylphenyl) ether 60 mg was dissolved in 20 ml of anhydrous ethanol solution of 5% acetic acid. After adding 30 mg of active carbon in 10% palladium thereinto, it was dissolved under hydrogen gas for 15 hours. Thus-obtained mixture Was washed with water and saturated sodium chloride aqueous solution. The resultant was dried with anhydrous magnesium sulfate and then concentrated.

2,6-diisopropylphenol 37 mg was obtained by separating the concentrate through a silica gel column chromatography with hexane/ethyl acetate (15:1) as a developing solvent.

NMR(CDCl$_3$): 1.30(12H, d, J=6), 3.17(2H, m), 6.90–6.98(1H, m), 6.88–7.13(3H, m).

EXAMPLE 2

0.5 g of 2-(1-methyl-2-propenyl)-6-isopropyl phenol which was obtained by means of Claisen rearrangement according to Example 1 was dissolved into acetic acid 8 ml and passed through ozone for 10 min in the rate of 60 mmol/hour at 15° C. with agitating. 2 ml of water was added into this reaction mixture and mixture was cooled down to 0° C. before 0.4 mg of zinc powder was added thereto. Thus-obtained mixture was agitated for 1 hour and then filtered.

The filtrate was dissolved into 40 ml of ether and washed four times with 10 ml of 10% sodium bicarbonate each time, and washed with water and saturated sodium chloride aqueous solution. The resultant was dried with anhydrous magnesium sulfate and then concentrated.

2,3-dihydro-7-isopropyl-3-methyl-2-benzofuranol 0.31 g was obtained by separating the concentrate through a silica gel column chromatography with hexane/ethyl acetate (10:1) as a developing solvent.

NMR(CDCl$_3$): 1.23(6H, d, J=6.2), 1.34(3H, d, J=6.6), 3.12-3.29(2H, m), 3.73(1H, b, s), 5.63(1H, b, s) 6.90-7.31(3H, m).

Colorless aqueous 2,6-diisopropylphenol 33 mg was obtained by reduction of obtained 2,3-dihydro-7-isopropyl-3-methyl-2-benzofuranol 50 ml in the similar manner as that described in Example 1.

NMR(CDCl$_3$): 1.30(12H, d, J=6), 3.17(2H, m), 6.90-6.98(1H, m), 6.88-7.13(3H, m).

What is claimed is:

1. A process for producing ortho-isopropylated phenol derivatives having following formula (VIII), the said process comprising the steps for:

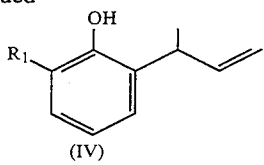

(a) producing a phenyl allyl ether having following formula (III) by reaction of a phenol derivative having following formula (I) and a crotyl derivative having following formula (II)

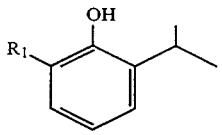

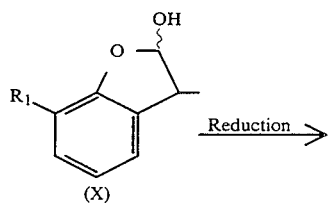

(in this reaction formula, R$_1$ is a hydrogen or a low alkyl group of C$_1$-C$_4$, X is chloride, bromide, iodide, para-toluene sulfonyl or methane sulfonyl)

(b) producing a phenol derivative having formula (IV) where allyl group of phenyl allyl ether (III) migrates to ortho position by means of Claisen rearrangement,

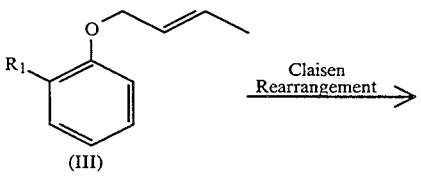

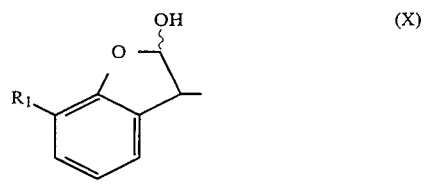

(c) producing a hemiacetal having following formula (X) by oxidation of the phenol derivative (IV), and

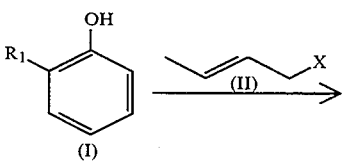

(d) producing an ortho-isopropylated phenol derivative (VIII) by reduction of the hemiacetal (X).

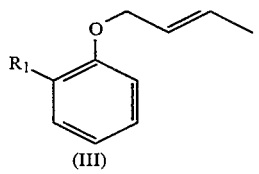

2. A process for producing ortho-isopropylated phenol derivatives as claimed in claim 1, wherein the reaction step (a) of a phenol derivative (I) and a crotyl derivative (II) is occured in a base-solvent system selected from the following base-solvent systems: a base-solvent system consisting of potassium carbonate, sodium carbonate, potassium bicarbonate or sodium bicarbonate as a base and polar solvent such as acetone, dimethylformamide or low alcohol as a solvent: a base-solvent system consisting of sodium ethoxide, sodium methoxide, sodium hydroxide, potassium hydroxide or lithium diisopropyl amine as a base and dry solvent such as tetrahydrofuran, ethyl ether, glyme, diglyme, low alkane or petroleum ether as a solvent: or base-solvent system consisting of sodium ethoxide or sodium methoxide as a base and alcoholic solvent such as ethanol, methanol as a solvent.

3. A process for producing ortho-isopropylated phenol derivatives as claimed in claim 1, wherein the said Claisen rearrangement is occured by heating with a solvent such as diethylaniline, dimethylaniline, ethylene glycol, propylene glycol or trifluoroacetic acid or without solvent.

4. A process for producing ortho-isopropylated phenol derivatives as claimed in claim 1, wherein the oxidation reaction of a phenol derivative (IV) produced by Claisen rearrangement is occured in the presence of an oxidation reagent such as ozone, osmium tetraoxide or potassium permanganate in a solvent such as acetic acid, mixture of acetic acid and acetonitrile, ethylacetate, ethanol, methanol or chloroform.

5. A process for producing ortho-isopropylated phenol derivatives as claimed in claim 1, wherein the reduction step (d) of oxidation product is occured by means of Wolff-Kishner reduction, Clemmensen reduction or hydrogenation.

6. A process for producing ortho-isopropylated phenol derivatives as claimed in any one of claims 1 to 5, wherein $R_1$ is isopropyl group.

7. A process for producing ortho-isopropylated phenol derivatives having following formula (VIII), the process comprising the steps for:

(VIII)

(a) producing a phenyl allyl ether having following formula (III) by reaction of a phenol derivative having following formula (I) and a crotyl derivative having following formula (II), (in this reaction formula, $R_1$ is a hydrogen or a low alkyl group of $C_1$–$C_4$, X is chloride, bromide, iodide, paratoluene sulfonyl or methane sulfonyl)

(b) producing a phenol derivative having formula (IV) where an allyl group of phenyl allyl ether (III) migrates to ortho position by means of Claisen rearrangement.

(e) producing a phenyl ether derivative having following formula (V) by protecting —OH group of the phenol derivative (IV), (in this formula, $R_2$ is methyl, acetyl, benzyl, trimethylsilyl or tert-butyl dimethylsilyl as a protecting group of —OH group)

(f) producing an aldehyde having following formula (VI) by oxidation of the phenyl ether derivative (V), (g) producing a phenyl ether derivative having following formula (VII) added an isopropyl group onto ortho position by reduction of the aldehyde (VI), and (h) producing an ortho-isopropylated phenol derivative (VIII) by eliminating protecting group from the phenyl ether derivative (VII).

8. A process for producing ortho-isopropylated phenol derivatives as claimed in claim 7, wherein the reaction step (a) of phenol derivative (I) and crotyl derivative (II) is occured in a base-solvent system selected from the following base-solvent systems; a base-solvent system consisting of potassium carbonate, sodium carbonate, potassium bicarbonate or sodium bicarbonate as a base and polar solvent such as acetone, dimethylformamide or low alcohol as a solvent; a base-solvent system consisting of sodium ethoxide, sodium methoxide, sodium hydroxide, potassium hydroxide or lithium diisopropyl amine as a base and dry solvent such as tetrahydrofuran, ethyl ether, glyme, diglyme, low alkane or petroleum ether as a solvent; or base-solvent system consisting of sodium ethoxide or sodium methoxide as a base and alcoholic solvent such as ethanol, methanol as a solvent.

9. A process for producing ortho-isopropylated phenol derivatives as claimed in claim 7, wherein the said Claisen rearrangement(b) is occured by heating with a solvent such as diethylaniline, dimethylaniline, ethylene glycol, propylene glycol or trifluoroacetic acid or without solvent.

10. A process for producing ortho-isopropylated phenol derivatives as claimed in claim 7, wherein the oxidation reaction (f) of a phenyl ether derivative (V) is occured in the presence of an oxidizing agent such as ozone, osmium tetraoxide or potassium permanganate in a solvent such as acetic acid, mixture of acetic acid and acetonitrile, ethyl acetate, ethanol, methanol or chloroform.

11. A process for producing ortho-isopropylated phenol derivatives as claimed in claim 7, wherein the reduction step (g) of aldehyde (VI) is occured by means of Wolff-Kishner reduction, Clemmensen reduction or hydrogenation.

12. A process for producing ortho-isopropylated phenol derivatives as claimed in any one of claims 7 to 11, wherein $R_1$ is isopropyl.

* * * * *